(12) United States Patent
O'Sullivan

(10) Patent No.: US 8,852,222 B2
(45) Date of Patent: Oct. 7, 2014

(54) SURGICAL BUR WITH ANTI-CHATTER FLUTE GEOMETRY

(75) Inventor: Denis F. O'Sullivan, Cloughoulamore (IE)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 13/402,579

(22) Filed: Feb. 22, 2012

(65) Prior Publication Data

US 2012/0158028 A1 Jun. 21, 2012

Related U.S. Application Data

(60) Division of application No. 12/691,918, filed on Jan. 22, 2010, now abandoned, which is a division of application No. 11/943,303, filed on Nov. 20, 2007, now abandoned, which is a continuation of application No. PCT/IB2006/002118, filed on Jul. 17, 2006.

(60) Provisional application No. 60/700,384, filed on Jul. 19, 2005, provisional application No. 60/866,735, filed on Nov. 21, 2006.

(51) Int. Cl.
  *A61B 17/32* (2006.01)
  *A61B 17/16* (2006.01)

(52) U.S. Cl.
  CPC ....... *A61B 17/32002* (2013.01); *A61B 17/1673* (2013.01); *A61B 17/1615* (2013.01)
  USPC ........................................................ 606/180

(58) Field of Classification Search
  USPC ......... 407/53, 54; 408/227–231; 606/80, 167, 606/170, 178, 180; 433/165, 166; 451/48; 15/104.05
  See application file for complete search history.

(56) References Cited

U.S. PATENT DOCUMENTS

| | | | | |
|---|---|---|---|---|
| 372,400 | A | * | 11/1887 | Browne ........................ 433/165 |
| 533,573 | A | | 2/1895 | Wilkens |
| 2,360,425 | A | | 10/1944 | Kinzbach |
| 2,411,209 | A | | 11/1946 | Furth et al. |
| 2,795,979 | A | | 6/1957 | Zerwick |
| 2,847,885 | A | | 8/1958 | Wagner |
| 3,337,936 | A | | 8/1967 | Curry |
| 3,409,965 | A | | 11/1968 | Fisher |

(Continued)

FOREIGN PATENT DOCUMENTS

| | | |
|---|---|---|
| DE | 3032493 A1 | 4/1982 |
| DE | 19718938 C1 | 11/1998 |
| DE | 19826276 C1 | 11/1999 |
| GB | 342881 A | 2/1931 |

OTHER PUBLICATIONS

"EPO ISA Search Report and Written Opinion" for PCT App. No. PCT/IB2006/002118, Nov. 2006.

*Primary Examiner* — David Eastwood

(57) ABSTRACT

A surgical bur including a shaft with a bur head. A number of flutes are formed on the bur head. Each flute has a cutting edge. Chamfer surfaces form the front, distally directed faces of some of the burs. The flutes without chamfer surfaces having cutting edges emerge from the bur head at locations relatively close to the distal end tip of the head. The flutes over which the chamfer surfaces extend have cutting edges that start, extend proximally rearward, from locations that are, spaced proximal from the distal end tip.

16 Claims, 24 Drawing Sheets

(56) References Cited

U.S. PATENT DOCUMENTS

| | | |
|---|---|---|
| 4,934,881 A | 6/1990 | Tsujimura et al. |
| 5,122,134 A | 6/1992 | Borzone et al. |
| 5,209,612 A | 5/1993 | Kish |
| 5,312,208 A * | 5/1994 | Shiga et al. .................. 408/224 |
| 5,618,293 A | 4/1997 | Sample et al. |
| 5,626,444 A | 5/1997 | Campian |
| 5,725,338 A | 3/1998 | Cabaret et al. |
| 5,759,185 A | 6/1998 | Grinberg |
| 5,833,402 A | 11/1998 | Martin |
| 5,888,200 A | 3/1999 | Walen |
| 5,913,867 A | 6/1999 | Dion |
| 6,158,304 A | 12/2000 | Packer et al. |
| 6,257,889 B1 | 7/2001 | Boston |
| 6,258,093 B1 | 7/2001 | Edwards et al. |
| 6,347,941 B1 | 2/2002 | Boston |
| 6,562,055 B2 | 5/2003 | Walen |
| 2004/0197741 A1 | 10/2004 | Mopper |
| 2005/0283160 A1 | 12/2005 | Knisely et al. |

* cited by examiner

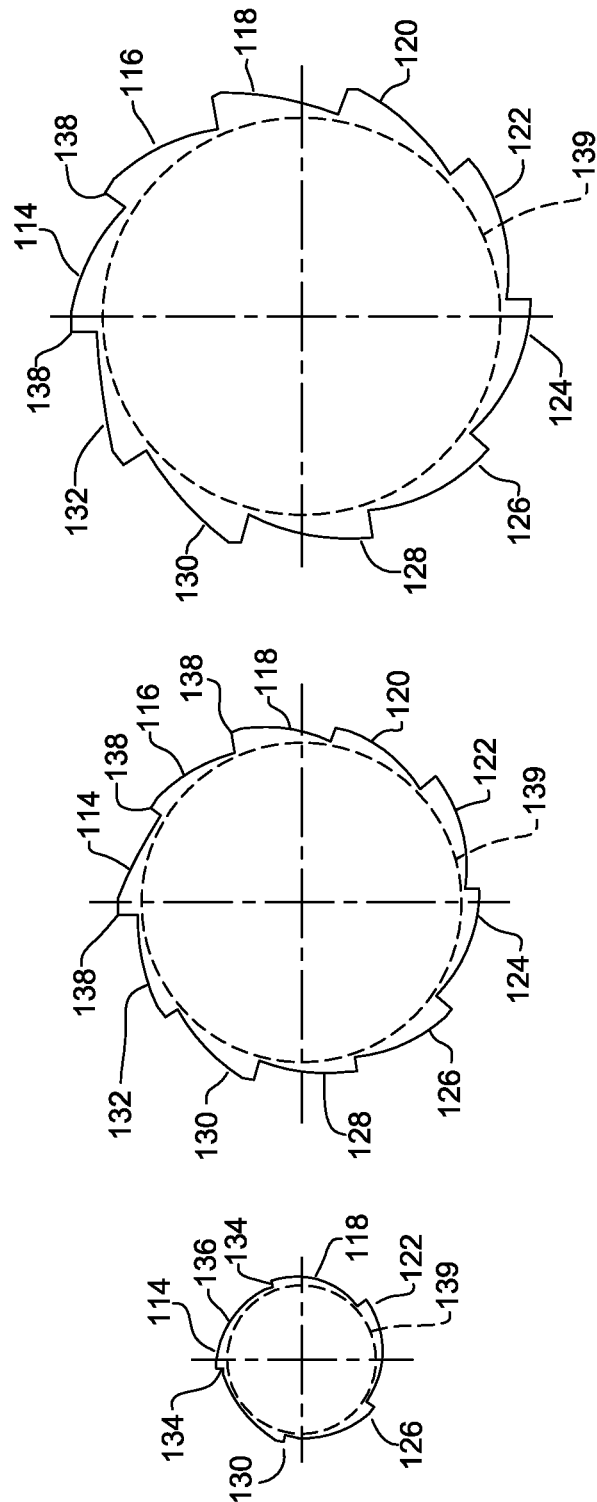

SURGICAL BUR WITH ANTI-CHATTER FLUTE GEOMETRY

RELATIONSHIP TO EARLIER FILED APPLICATIONS

This application is a divisional of U.S. patent application Ser. No. 12/691,918, filed 22 Jan. 2010, now abandoned. application Ser. No. 12/691,918 is a divisional of application Ser. No. 11/943,303 filed 20 Nov. 2007, now abandoned. application Ser. No. 11/943,303 is a continuation of PCT App. No. PCT/IB2006/002118, filed 17 Jul. 2006 which claims priority from U.S. Pat. App. No. 60/700,384 filed 19 Jul. 2005. Application Ser. No. 11/943,303 also claims priority from U.S. Pat. App. No. 60/866,735 filed 21 Nov. 2006. The contents of the priority applications are hereby explicitly incorporated herein by reference.

BACKGROUND OF THE INVENTION

This invention is generally related to surgical burs. More particularly, this invention is related to a surgical bur with a bur head geometry that substantially reduces chatter when the bur is applied to a surgical site.

BACKGROUND OF THE INVENTION

A tool used to perform a surgical procedure is the bur. A bur generally consists of a head formed from rigid material, typically metal, shaped to have a number of flutes. The flutes are formed to define tissue cutting edges. A shaft extends rearwardly from the head. The free end of the shaft has a feature that facilitates locking the shaft to a powered handpiece. The actuation of the handpiece results in the rotation of the bur. During a surgical procedure, the bur head is placed against a surgical site where a section of tissue is to be removed. The rotating cutting edges excise tissue away from the surgical site. Burs of various shapes and sizes are used in procedures such as orthopedic surgery, neuro and spinal surgery, ear noise and throat surgery and in other surgical procedures in which a sub-procedure is to selectively remove a section of tissue.

Burs work well for the purposes for which they are designed. Nevertheless, a problem associated with some burs is chatter. Chatter is the back and forth vibration of a bur head against the surface to which the bur head is applied. Chatter occurs as a result of bur's individual cutting edges repeatedly being forced against the tissue against which the bur head is applied. Generally, there three reasons a bur may start to chatter.

One reason a bur starts to chatter is because it receives an input of energy due to a process known as regeneration of waviness. This process is due to the fact that when a cutting edge passes across a section of tissue, it leaves a specific wavy (essentially sinusoidal) profile along the surface of the tissue. If two adjacent cutting edges cut in phase, the second cutting edge excises tissue along a surface profile identical to that along which in was excised by the first flute. In practice, due to the invariable movements of the bur head and the tissue, this does not happen. When any two successive cutting edges pass over the same tissue section, the second flute cutting edge removes tissue on a path that does not overlap the tissue wave excised by the first cutting edge. Consequently, the debris chips cut by the second cutting edge have variable thickness. This means, during the process in which the second cutting edge excises the chip from the tissue, the cutting edge and its flute are subjected to variable forces. Over time, the repetitive exposure of the bur flutes to these variable forces causes the bur to undergo forced vibration.

A second reason a bur may chatter is that it is rotated at its resonant frequency. If this occurs, the repetitive force against the flutes self-excites the bur to move back and forth through a continually increasing range of motion.

The third reason a bur may chatter is due to the depth of the cut in the tissue against which the bur head is applied. If a bur head is pressed against the tissue so as to make only a relatively shallow cut, the overall time any two adjacent flutes are exposed to the tissue being cut is relatively low. The time in which the two adjacent flutes, as well as the spatial gap between the flutes, are exposed to the open environment is relatively high. During these relatively long time periods, tissue cut from bur and entrained in this gap is able to be discharged away from the bur head. This gap is then relatively debris-free the next time it rotates against the in-place tissue. Additional newly excised tissue fills this gap. However, if the bur head is pressed against the tissue to make a deep cut, the time in which the spatial gap between any two flutes is located against the in-place tissue increases. The time this gap is exposed to the open environment drops. Consequently, there may not be enough time for tissue entrained in this gap to be discharged. These gaps between the flutes clog. If this occurs, during the next time period in which the gap is rotated against the in-place. It is believed that that build up of chips between the flutes and their cutting edges clogs the bur head. This clogging, in turn, it is believed causes a forced vibration and the resultant chatter.

SUMMARY OF THIS INVENTION

This invention is directed to the design of a new and useful surgical bur. The bur of this invention is provided with cutting edges positioned to reduce, if not eliminate, chatter that occurs during the use of the bur.

The bur of this invention has plural sets of flutes. Each flute defines a cutting edge, an edge that removes tissue from the surgical site to which the bur is applied. The flutes in a first set of flutes are shaped to have cutting edges that emerge from the body of the bur head at a first position relative to the distal end tip of bur head. Often, but not always, these cutting edges emerge from the distal end tip. The flutes in the second set of flutes are shaped to have cutting edges that emerge from the bur head body at a second position spaced proximally from the first position.

In some versions of the invention, the distal ends of the second set of flutes are chamfered. As a result of the chamfers, the cutting edges of the flutes start at positions proximal to the distal ends of the flutes.

In some versions of the invention, the bur head is formed so that the second set of flutes emerges from the bur head at locations proximal to the locations from which the first set emerges.

BRIEF DESCRIPTION OF THE DRAWINGS

The invention is pointed out with particularity in the claims. The above and further features of this invention may be better understood by reference to the following detailed description taken in conjunction with the accompanying drawings in which:

FIG. 13 is a cross section view of the bur head of FIG. 12 taken along line 13-13;

FIG. 14 is a cross section view of the bur head of FIG. 12 taken along line 14-14;

FIG. 15 is a cross section view of the bur head of FIG. 12 taken along line 15-15;

DETAILED DESCRIPTION

Figure 1:
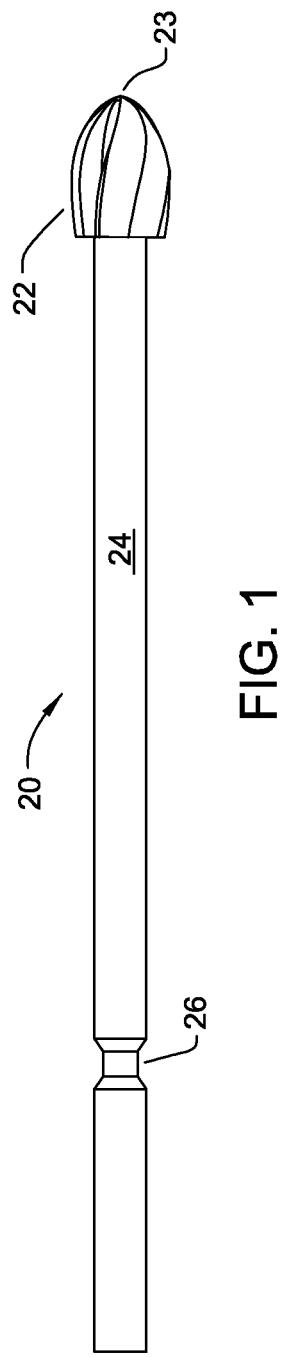
FIG. 1 is a side view of a basic surgical bur constructed in accordance with this invention.

FIG. 1 illustrates a surgical bur 20 constructed in accordance with this invention. Bur 20 has a head 22 that forms the distal end of the bur. ("Distal" it shall be understood, means towards the surgical site to which the bur is applied. "Proximal" means away from the surgical site.) Bur head 22 has a distal end tip 23 that is the most forward portion of the bur 20. A shaft 24 extends proximally rearward from the bur head 22.

Figure 1A:
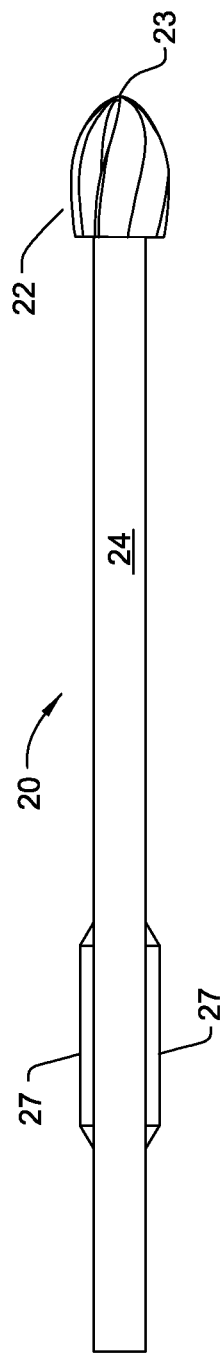
FIG. 1A is a side view of an the surgical bur of this invention illustrating an alternative geometric feature for coupling the shaft to a surgical handpiece.

The proximal end of the shaft 24 is provided with coupling features 26. The coupling features 26 are geometric features that facilitate the removable engagement of the shaft 24 to a coupling assembly integral with the rotating shaft of a powered surgical tool with which bur 20 is used (tool not illustrated.) The illustrated coupling features 26 are a set of planar faces recessed relative to the outer diameter of the shaft 24. One such geometry is described and illustrated in U.S. Pat. No. 5,888,200, issued 30 Mar. 1999, Multi-Purpose Surgical Tool System, the contents of which is incorporated herein by reference. An alternative geometry for coupling features 26 in the form of linearly aligned opposed concave surfaces is illustrated in U.S. Pat. No. 6,562,055, issued 13 May 2003, Cutting Attachment For A Surgical Handpiece Designed To Be Selectively Coupled To The Handpiece, the contents of which is incorporated herein by reference. It should be appreciated that these two geometries of coupling features are exemplary, not limiting. In alternative versions of the invention, these coupling features may for example, be threading. Alternatively, as depicted in FIG. 1A, tabs 27 that project outwardly from the outer surface of shaft 24 may function as the coupling features. The exact geometry of the coupling feature is not relevant to the structure of this invention.

Figure 2A:
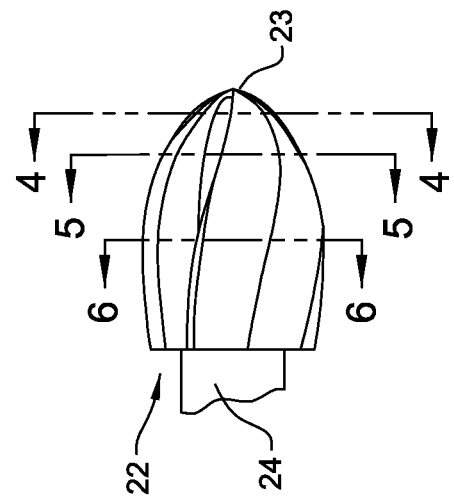
FIGS. 2 and 2A are enlarged side views of a bur head shaped in accordance with this invention.
Figure 2:
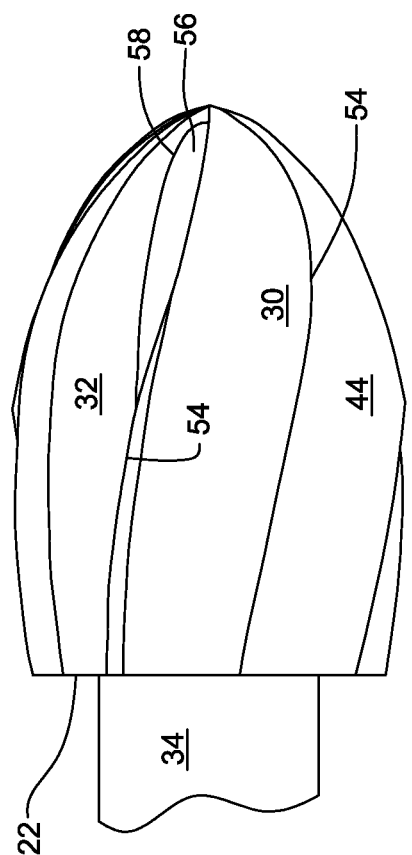
Figure 3:
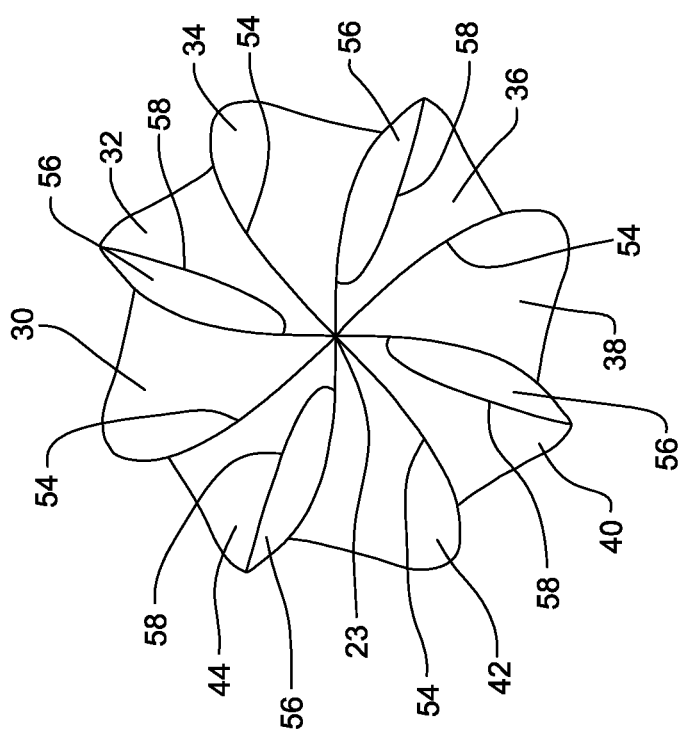
FIG. 3 is a front view, looking proximally rearward, of the bur head of FIG. 2.
Figure 4:
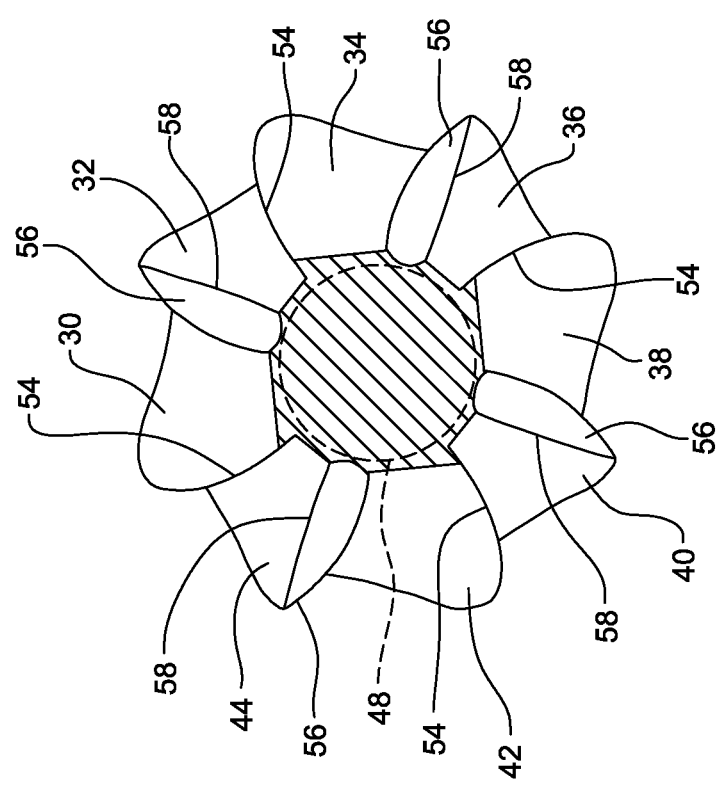
FIG. 4 is a cross sectional view of the bur head of FIG. 2 taken along line 4-4 of FIG. 2A.
Figure 5:
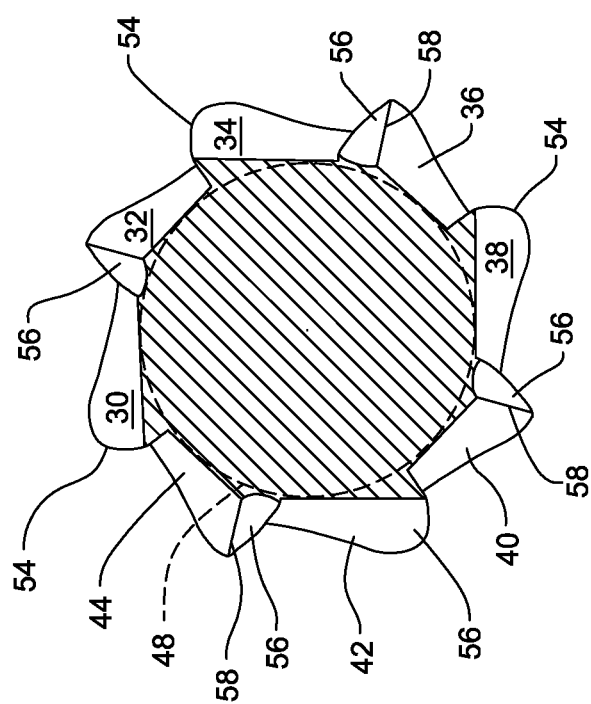
FIG. 5 is a cross sectional view of the bur head of FIG. 2 taken along line 5-5 of FIG. 2A.
Figure 6:
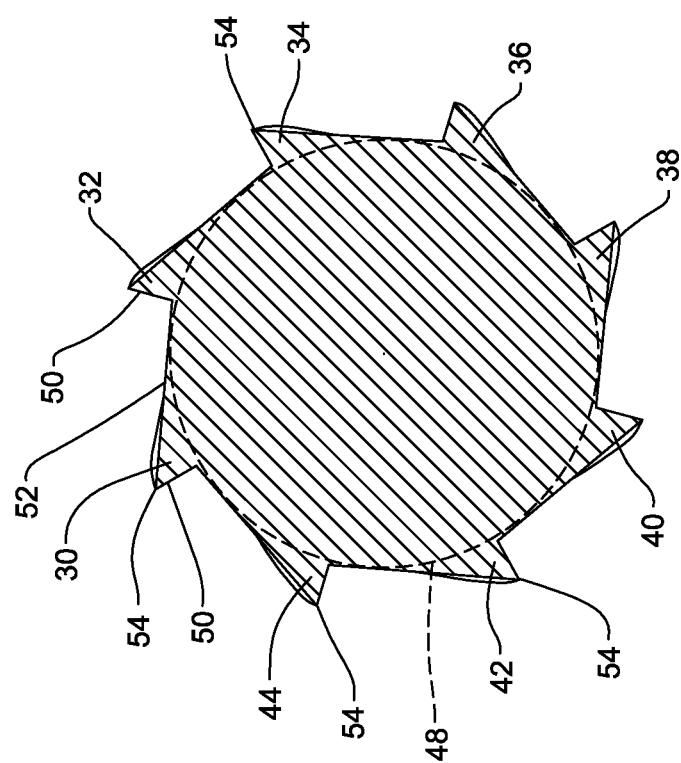
FIG. 6 is a cross sectional view of the bur head of FIG. 2 taken along line 6-6 of FIG. 2A.
Figure 7:
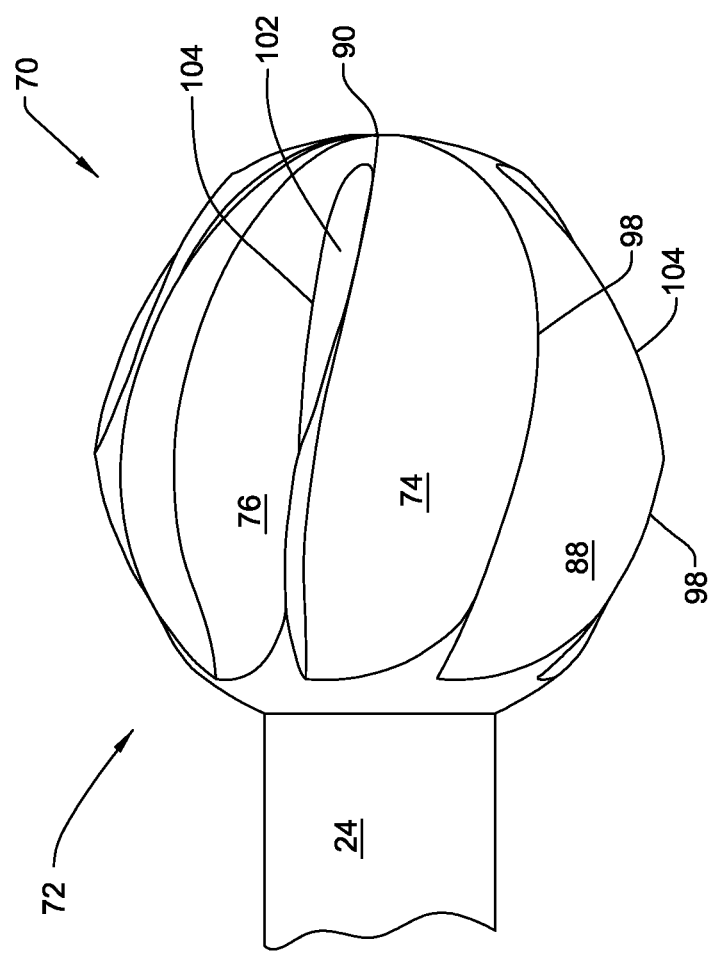
FIGS. 7 and 7A are side views of an alternative bur head constructed in accordance with this invention.
Figure 7A:
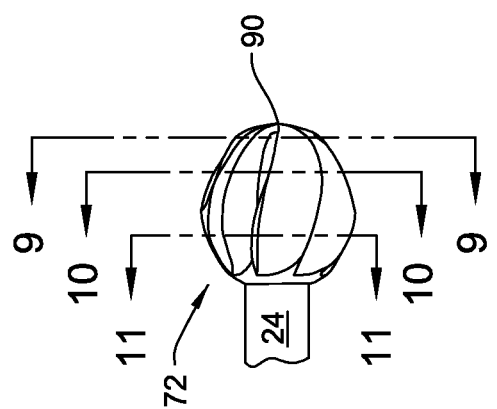

Bur head 22, as seen best in FIGS. 2, 2A and 3, is formed with a number of arcuately spaced flutes 30-44. Each flute 30-44, as seen by the cross sectional view of flute 30 in FIG. 6, is formed by a rake surface 50 and a clearance surface 52. Rake surface 50 extends approximately radially from the longitudinal axis of the center core of the bur head 22. In the Figures, the outer perimeter of the center core is generally represented by dashed circle 48. It should be understood that, as the outer diameter of the bur changes along the length of the bur, the outer diameter of the center core changes. Each clearance surface 52 extends generally tangentially from the outer perimeter of the bur head center core. More specifically, each clearance surface 52 extends approximately tangentially away from the base of the rake surface 50 of the flute adjacent the flute formed by the clearance surface. Thus, the clearance surface 52 of flute 30 extends from the position along the perimeter of the bur head core from which rake surface 50 of flute 32 extends.

The rake surface 50 and clearance surface 52 that form an individual flute meet to forming a cutting edge 54. The bur cutting edges 54 are the edges of the bur head 22 that perform the cutting when the bur 20 is applied to a surgical surface.

As seen best by FIG. 3, bur head 22 of this invention, flutes 30, 34, 38 and 42 are formed so that their rake and clearance surfaces 50 and 52, respectively, meet to form cutting edges 54 that start at a location relatively close to the distal end tip 23 of the bur head. Flutes 32, 36, 40 and 44 are formed so that, at the distal ends of the flutes, chamfer surfaces 56, angled from the rake surfaces 50, extend between the rake surfaces 50 inwardly towards and to the clearance surfaces 52. Flutes 32, 36, 40 and 44 thus have chamfer edges 58 that are the edge surfaces along the interfaces between the clearance surfaces 54 and chamfer adjacent chamfer surfaces 56. As seen by FIGS. 2, 4, 5 and 6, chamfer surfaces 56 are formed on flutes 32, 36, 40 and 44 to end at the points along the flutes where the flutes have the largest outer diameter relative to the longitudinal center axis of the bur 20.

Bur head 22 may be formed by first shaping the head to provide eight (8) identical flutes that extend the full length of the head from the distal end tip to the shaft. Then portions of flutes 32, 36, 40 and 44 are selectively removed to form chamfer surfaces 52. Grinding, electro-discharge machining or laser cutting or other machining methods may be employed to excise the material from flutes 32, 36, 40 and 44 to form chamfer surfaces 56.

Owing to the presence of the chamfer surfaces 56, at any location along the longitudinal axis of the bur head where some flutes have cutting edges 54 and other flutes chamfer edges 58, the chamfer edges 58 are closer to this axis than cutting edges 54. Thus, chamfer edges 58 do not cut the tissue against which the bur head 22 is applied.

When a surgeon applies a bur 20 to a surgical site, often the section of the bur adjacent the distal end tip 23 is the section of the bur head 22 that is pressed against the tissue to be excised. It is at this time the above-described geometry of the bur of this invention becomes advantageous. There are a reduced number of cutting edges 54 at the distal end tip 23. It is believed this reduces the extent to which forces generated as a result of regeneration of waviness excite the bur into chatter vibration. Moreover, since there are a reduced number of cutting edges 56 at the most distal section of the bur head 22, the interstitial gap between cutting edges is wider than it would be otherwise. The relatively large size of these gaps minimizes the extent to which excised tissue is trapped in these spaces. This reduces the extent to which tissue entrained in the inter-flute gaps imposes addition vibration-causing force on the bur head 22.

The reduction of the number of cutting edges also reduces the tooth passing frequency at the distal tip of the bur 20. This is the frequency at the cutting edges 54 press against the tissue being excised. This frequency, TPF, is calculated according to the formula:

$$TPF = [RPM \times \text{No. of } CE]/60$$

Here, RPM is the revolutions per minute of the bur 20. Variable CE is the number of bur head 22 cutting edges at the position along the bur head at which the bur head is being applied to the tissue to be excised. With bur head 22 of this invention, since there are fewer cutting edges at the distal end of the bur head 22 than at more proximal locations, the tooth passing frequency at the distal end locations is less than the tooth passing frequency at the more proximal locations along the length of the bur head.

This reduction in distal end tooth passing frequency further reduces the chatter of bur 20 of this invention. This is because a further means of reducing chatter is to operate the bur at a speed so that the tooth passing frequency as closely as possible matches the chatter frequency. This frequency matching assists in the nulling of bur chatter vibration. By reducing the number of flute cutting edges 54 at the distal end of the bur head 22, it is more likely that when, this end of the bur head is pressed against tissue, the tooth passing frequency will more closely approximate the chatter vibration frequency.

Bur head 22 of bur 20 has what is referred to as an acorn style head. As depicted by FIGS. 7, 7A and 8-11, this invention may be incorporated into bur heads having alternative shapes. Specifically, bur 70 of this version of the invention has what is referred to as a round or spherical head 72. As seen by reference to FIG. 8, bur head 72 has flutes 74-88. Each of the flutes 74-88 originate at the distal end tip 90 of bur head 72.

Figure 11:
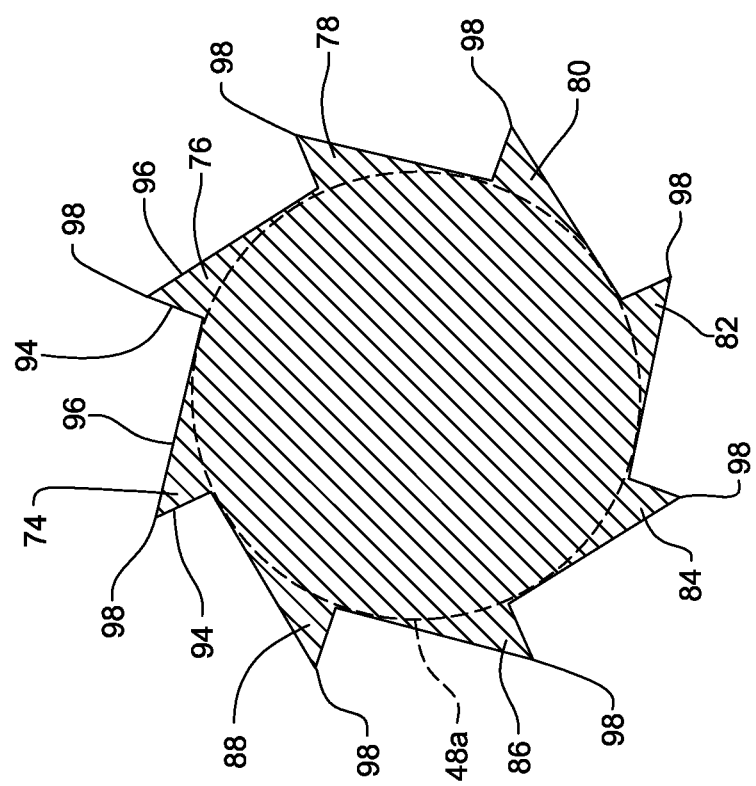
FIG. 11 is a cross sectional view of the bur head of FIG. 7 taken along line 11-11 of FIG. 7A.

Each flute 74-88, as best seen in FIG. 11, is formed with both a rake surface 94 and a clearance surface 96. Flutes 74, 78, 82 and 86 are formed to have cutting edges 98 that, like the flutes themselves, originate at the distal end tip 90 of the bur head.

Figure 8:
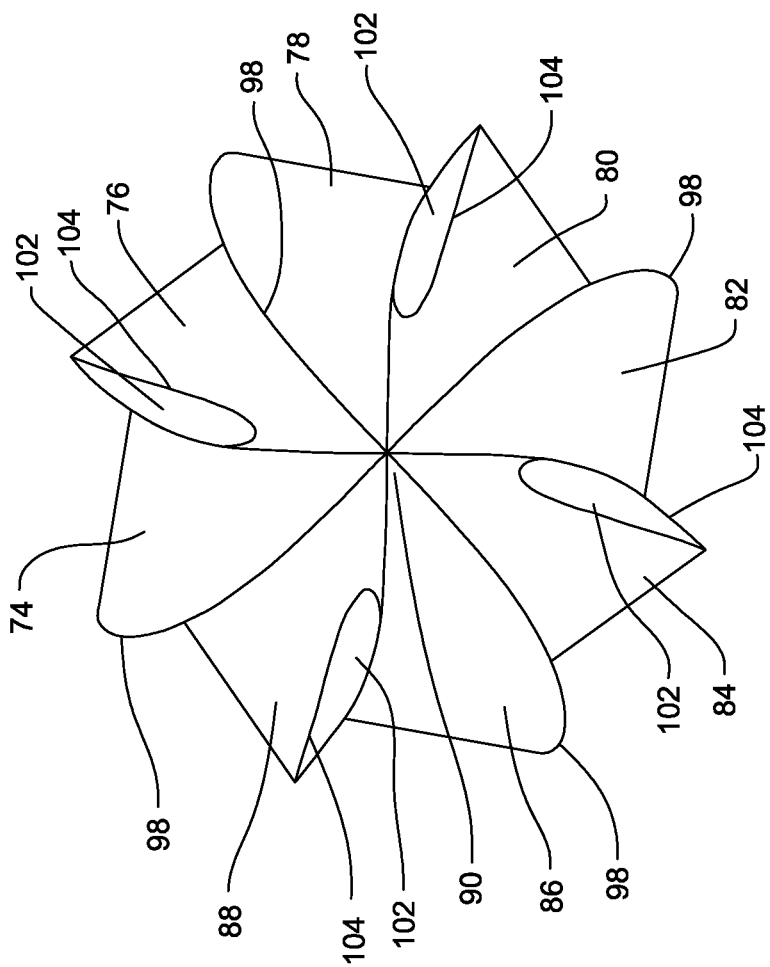
FIG. 8 is a front view, looking proximally rearward, of the bur head of FIG. 7.
Figure 9:
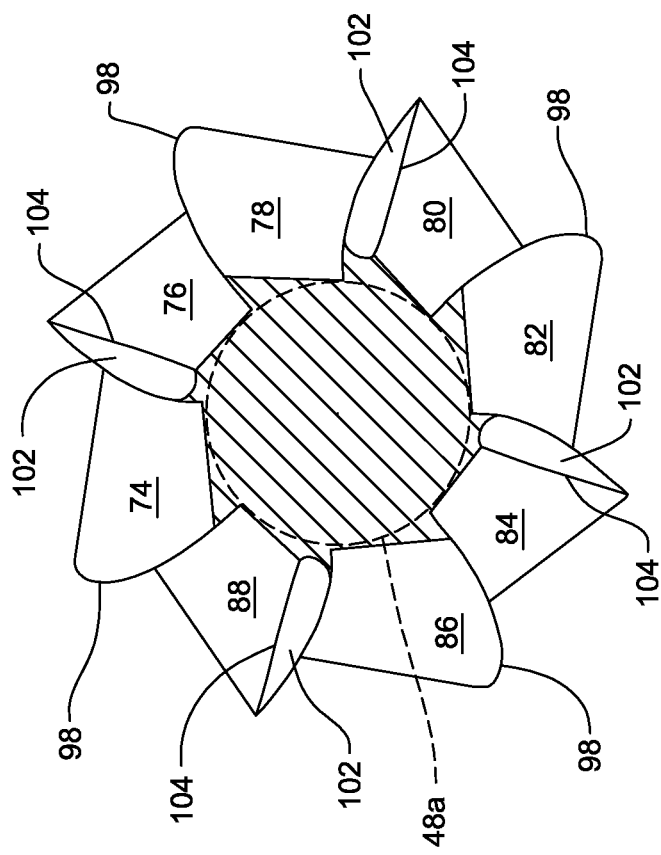
FIG. 9 is a cross sectional view of the bur head of FIG. 7 taken along line 9-9 of FIG. 7A.
Figure 10:
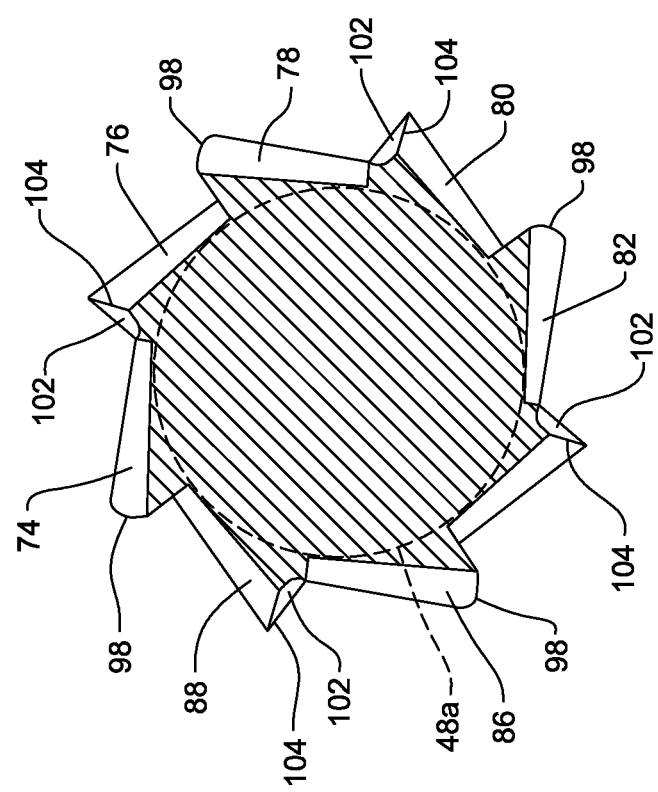
FIG. 10 is a cross sectional view of the bur head of FIG. 7 taken along line 10-10 of FIG. 7A.

Flutes 76, 80, 84 and 88 are formed with chamfer surfaces 102, best seen in FIGS. 8, 9 and 10, that start adjacent bur head distal end tip 90. Flutes 76, 80, 84 and 88 thus are formed with chamfer edges 104 where each clearance surface 96 meets the associated flute chamfer surface 102. Chamfer surfaces 102 are formed on flutes 76, 80, 84 and 88 so that chamfer edges 104 terminate and cutting edges 98 begin at the point where the bur head has its largest outer diameter.

FIGS. 12-15 illustrate another bur 110 constructed in accordance with this invention. Bur 110 has a spherical bur head 112. Bur head 112 is shaped to have ten (10) flutes 114-132 best seen in FIG. 15. Each flute 114-132 has a rake surface 134 and a clearance surface 136. The rake and clearance surfaces 132 and 134, respectively, of each flute 114-130 meet to form a cutting edge 138 that extends along the length of the flute.

Bur head 112 of this invention is formed so that the flutes originate from the core of the bur head, represented by dashed circles 139 at different positions along the length of the bur head. FIG. 13, for example, illustrates the flutes present at a position adjacent distal end tip 140 of bur head 112. It can be seen here that only flutes 114, 118, 122, 126 and 130 have emerged from the core of bur head 112. Thus, clearance surface 136 of flute 130 emerges from the base of rake surface 134.

Extending proximally along the bur head 112, away from the distal end tip 140, flutes 116, 120, 124, 128 and 132 start to emerge from the core of bur head 112 as seen in FIG. 14. Initially the rake surfaces 134 of flutes 116, 120, 124, 128 and 132 are shorter in length than the length of rake surfaces 134 of flutes 114, 118, 122, 126 and 130. Thus, the cutting edges 138 of flutes 116, 120, 124, 128 and 132 are spaced inwardly of the cutting edges of flutes 114, 118, 122, 126 and 130. Consequently, at the bur head position of line 14-14 of FIG. 12, cutting edges 138 of flutes 116, 120, 124, 128 and 132 do not contribute to the cutting of the tissue to which the bur 110 is applied.

Figure 12:
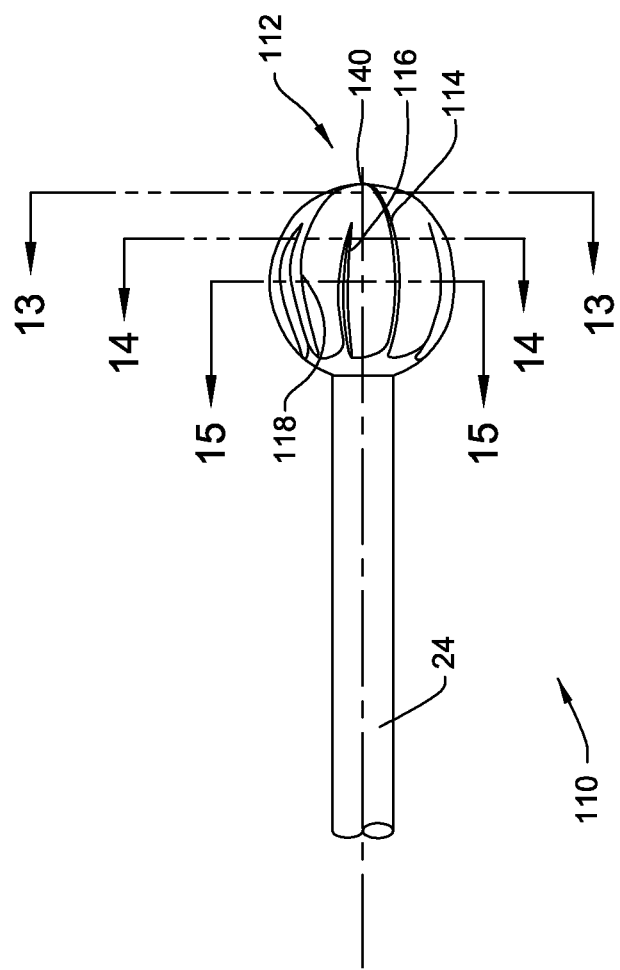
FIG. 12 is a side view of a second alternative bur head constructed in accordance with this invention.

As seen by FIGS. 12 and 15, at the position along the length of the bur head 112 where the head is of largest diameter, flutes 116, 120, 124, 128 and 132 are fully emerged from the head core. All flutes 114-132 are of equal height relative too the perimeter of the bur head core. Thus the cutting edges 138 all contact, and therefore cut, the tissue against which this section of the bur is placed.

This version of the invention may be constructed by first forming bur head 112 so that all the flutes extend the full length of the bur head. Then material is removed from flutes 116, 120, 124, 128 and 132 so that the flutes emerge from the bur head core at a position proximal to the distal end tip 140. The means used to form chamfer surfaces 56 are employed to similarly shape flutes 116, 120, 124, 128 and 132.

Figure 16:
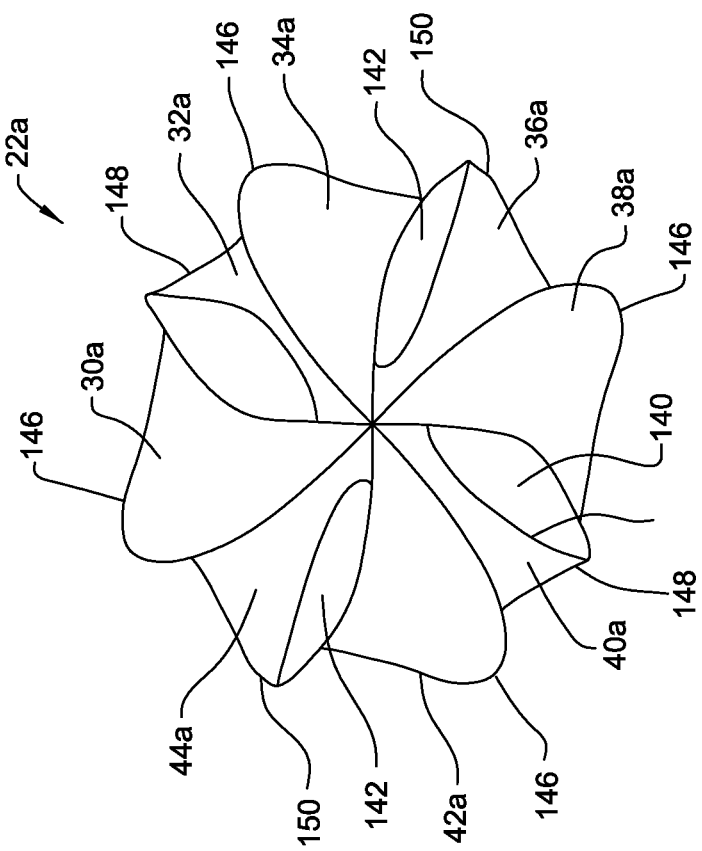
FIG. 16 is a front view, looking proximally rearward of a third alternative bur constructed in accordance with this invention.

FIG. 16 represents an alternative version of the invention of FIGS. 1-6. In this version of the invention bur head 22a is formed with flutes 30a-44a. Flutes 30a, 34a, 38a and 42a are not formed with chamfered surfaces. Flutes 32a and 40a are formed with chamfered surfaces 140. Flutes 36a and 44a are formed with chamfered surfaces 142. Flutes 32a and 40a are formed so that chamfered surfaces 140 extend a first distance proximally rearward along the length of bur head 22a. Flutes 36a and 44a are formed so that chamfered surfaces 142 extend a second distance proximally rearward along the length of the bur head 22a. This second distance is greater than the first distance chamfered surfaces 140 extend. Thus, bur head 22a of this embodiment of the invention is constructed to have a first set of cutting edges 146, where the clearance and rake surfaces of flutes 30a, 34a, 38a and 42a meet, which emerge from the core of the bur head at a first location along the length of the bur head. A second set cutting edges 148, where the clearance surfaces and chamfered surfaces 140 of flutes 32a and 40a meet, emerges from the core of the bur head at a second location along the length. A third set of cutting edges 150, where the clearance surfaces and chamfered surfaces of flutes 36a and 44a meet, emerges at a third location along the length of the bur head. This third location is, relative to the distal end tip, spaced further away than the second location.

Figure 18:
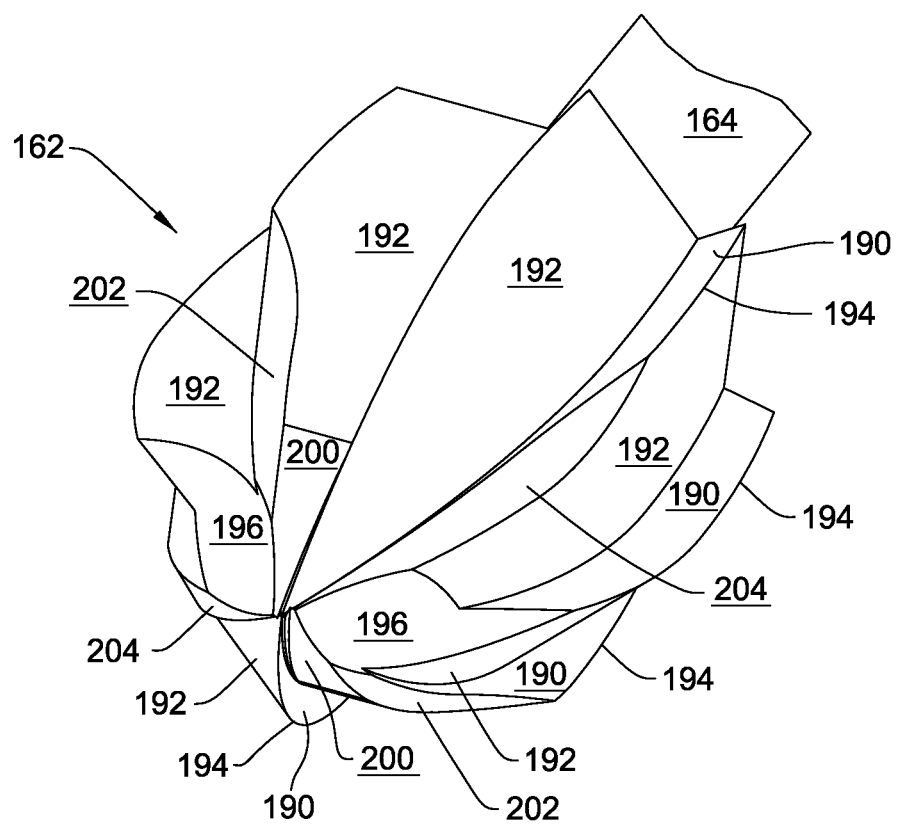
FIG. 18 is an isometric view of an alternative bur of this invention.
Figure 19:
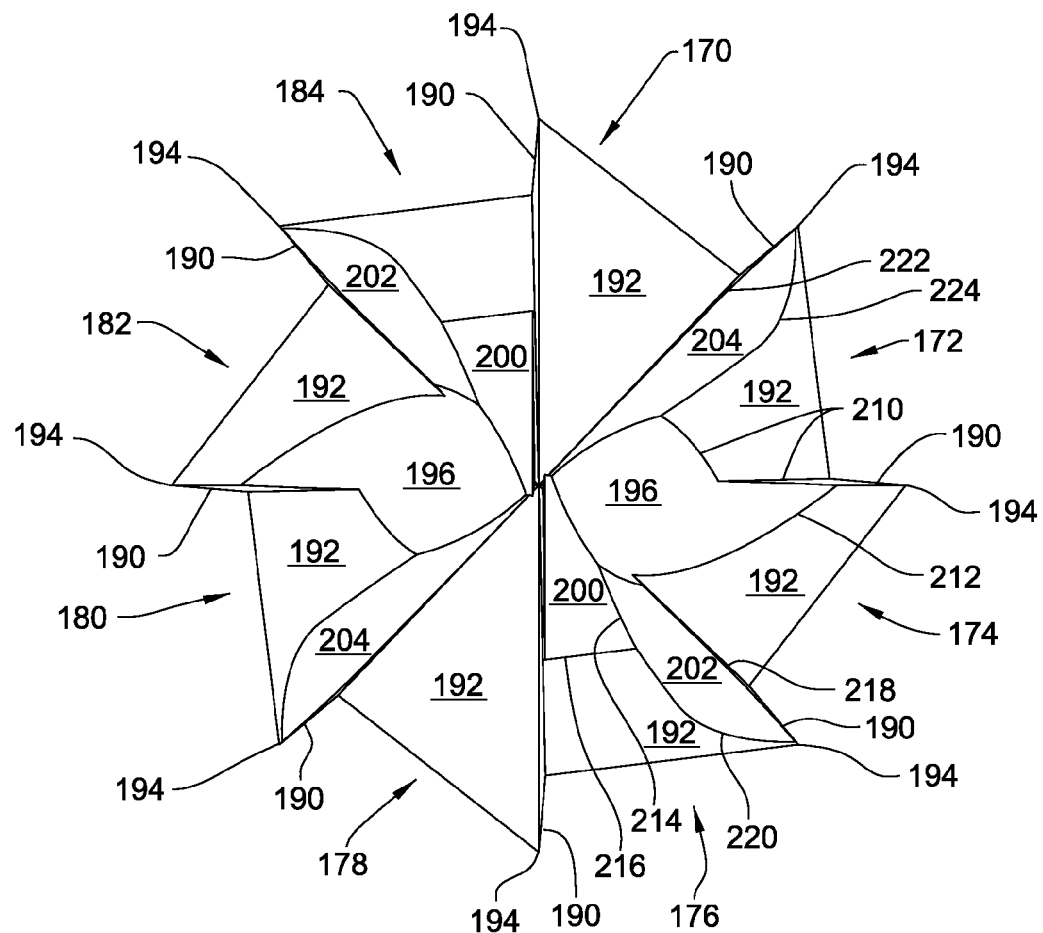
FIG. 19 is a front view of the bur head of FIG. 18 showing respective flute chamfers and cutting edges.

FIG. 18 illustrates another surgical bur 160 constructed in accordance with this invention. Bur 160 has a head 162 with a distal end tip 163. As seen in FIGS. 18 and 19, bur head 162 is formed with a number of arcuately spaced flutes 170-184.

Figure 22:
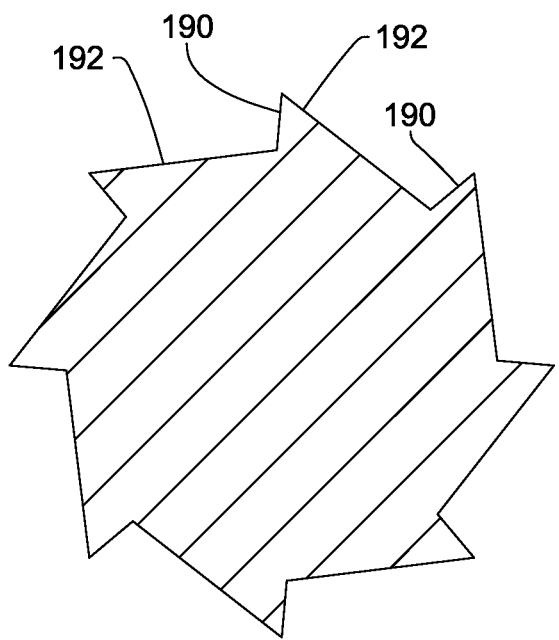
FIG. 22 is a cross sectional view of the bur head of FIG. 18.

Each flute 170-184, as seen by the front view of flute 170 in FIG. 3, is formed by a rake surface 190 and a clearance surface 192 (FIG. 22). Rake surface 190 extends approximately radially from the longitudinal axis of the center core of the bur head 162. It should be understood that, as the outer diameter of the bur changes along the length of the bur, the outer diameter of the center core changes. Each clearance surface 192 extends generally tangentially from the outer perimeter of the bur head center core. More specifically, each clearance surface 192 extends approximately tangentially away from the base of the rake surface 190 of the flute adjacent the flute formed by the clearance surface. Thus, the clearance surface 192 of flute 170 extends from the position along the perimeter of the bur head core from which rake surface 190 of flute 172 extends.

The rake surface 190 and clearance surface 192 that form an individual flute meet to form a cutting edge 194. The bur cutting edges 194 are the edges of the bur head 162 that perform the cutting when the bur 160 is applied to a surgical surface.

Figure 20:
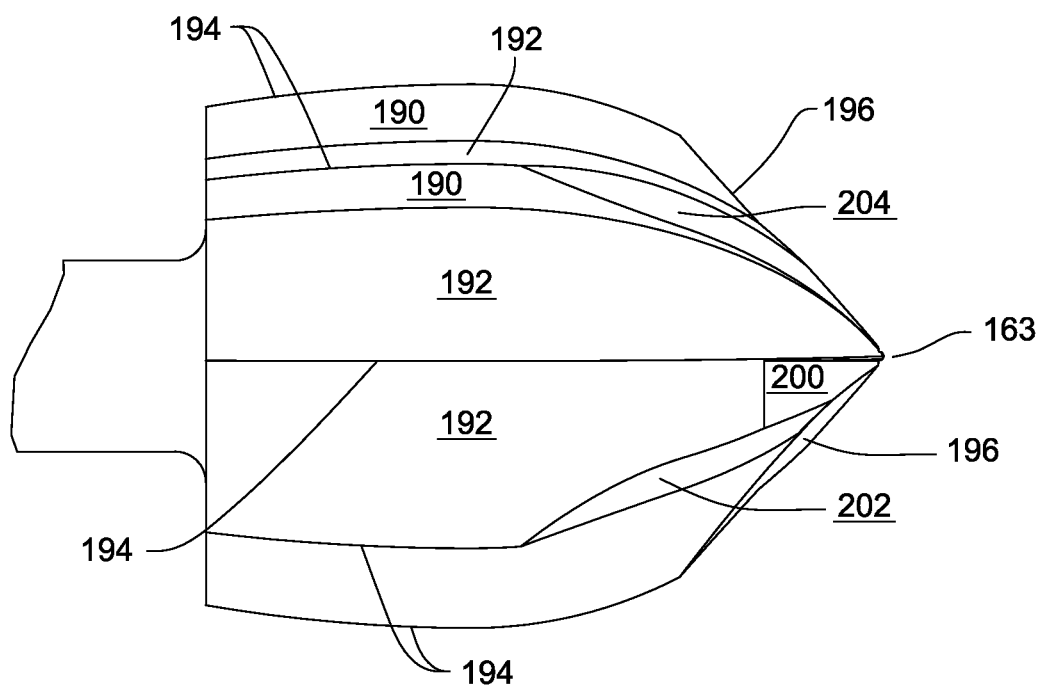
FIG. 20 is a side view of the bur head of FIG. 18 shaped in accordance with this invention.
Figure 21:
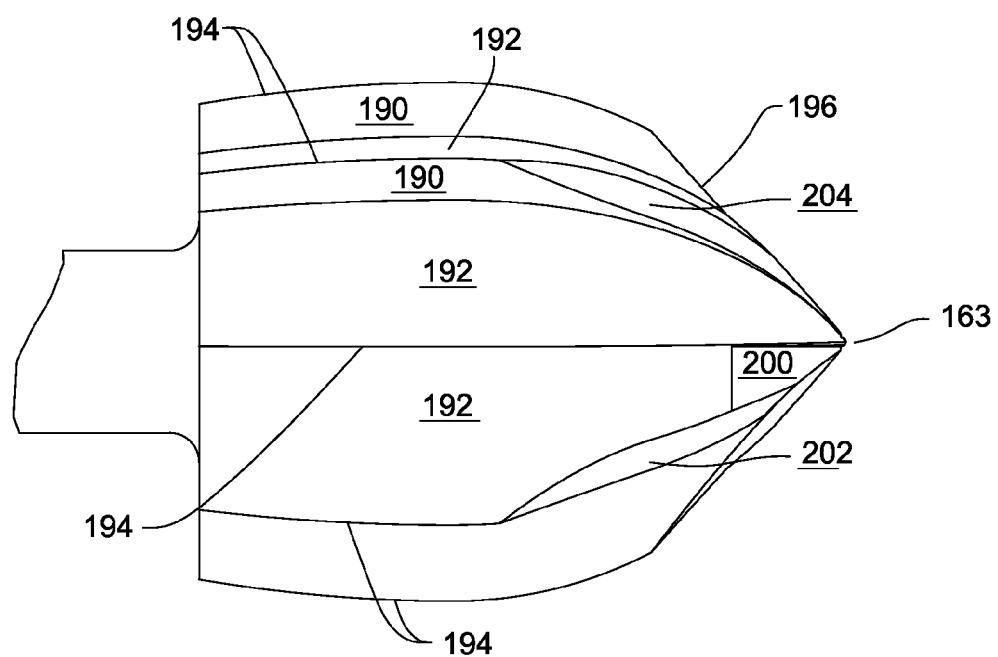
FIG. 21 is a side view of the bur head of FIG. 18, rotated along the axis of the bur.

As seen best in FIGS. 19-21, bur head 162 of this invention, has a first pair of two flutes, flutes 170 and 178, that are formed so that their rake and clearance surfaces 190 and 192, respectively, meet to form cutting edges 194 at a location that starts relatively close to the bur head distal end tip 163. More specifically, the area on the surface of the bur immediately around tip 163 can be considered to be a land that is fluteless. Flutes 170 and 178, including their cutting edges 194, emerge from this land. Flutes 170 and 178 are also symmetrical to one another, 180° apart.

Within each arcuate section of the bur head between flutes 170 and 178 there are plural additional flutes. In one section there are flutes 172, 174 and 176. The second arcuate section contains flutes 180, 182 and 184. Flutes 172 and 184 are radially adjacent flute 170. Flutes 174 and 182, which are symmetric around the longitudinal center axis of the bur head 162, are radially spaced from both flutes 170 and 178. These intermediate sets of flutes 172-176 and 180-184 are formed with chamfers surfaces. These chamfer surfaces effectively "cut-off" the cutting edges of flutes 172-36 and 180-184 so that their cutting edges 194 emerge from the bur head at locations spaced from the distal end tip of 163 the bur head 162.

There is a common chamfer surface, surface 196 over each set of flutes 172-176 and 180-186. Each of the chamfer surfaces 196 forms the common distal end face of one of the intermediate flute sets, flute set 172-176 and flute set 180-186. Each chamfer surface 196 starts at the distal at the perimeter of the land at the distal end tip of the bur head. Chamfer surfaces 196, relative to the cutting edges 194 of flutes 170 and 178 are angled closer to the proximal end of the bur shaft. Thus, the presence of chamfer surfaces 196 means that the cutting edges of flutes 172-176 and 180-186 emerge from the bur head at distances that are spaced proximal to the distal end tip of the bur head.

Symmetrically opposed flutes 176 and 184 each have a chamfer surface 200. Each chamfer surface 200 emerges from adjacent the distal end tip of the bur head. Thus each chamfer surface 200 forms an edge with an adjacent chamfer surface 196. Each chamfer surface 200 also abuts the distal end rake surface 190 of one of the flutes 170 or 178. Each chamfer surface 200 has an angle from the longitudinal axis of the bur shaft than the angle of the adjacent chamfer surface 196.

Each flute 176 and 184 is formed with a second chamfer surface, chamfer surface 202. Each chamfer surface 202 extends distally rearward from the point where the abutting chamfer surfaces 196 and 200 move apart from each other. Thus, each chamfer surface 202 extends between the rake and clearance surfaces 190 and 192, respectively, of the associated flute 176 or 184.

Each chamfer surface 202 extends proximally rearward along the bur head further than the associated chamfer surface 196. Owing to the presence of chamfer surfaces 202, the cutting edges 194 of flutes 176 and 184 emerge from the bur head at position proximal to those where cutting edges 194 of symmetrically opposed flutes 174 and 182 emerge.

Each flute 172 and 180 is formed with its own chamfer surface 204. Each chamfer surface 204 starts at a point a short distance proximally rearward from the distal end tip of the bur head, at the perimeter of the land. Each chamfer surface 204 extends between the rake and clearance surfaces 190 and 192, respectively, of the associated flute 172 or 180. The distal portion of each chamfer surface 204 intersects the adjacent chamfer surface 196.

Each chamfer surface 204 extends rearward along the associated flute 172 or 180 a distance approximately equal to the distance along which chamfer surfaces 202 extend. (These distances being from the distal end tip of the bur head.) Thus, owing to the presence of chamfer surfaces 204, cutting edges 194 of flutes 172 and 180 emerge from the bur head at the approximately the same position at which the cutting edges 194 of flutes 176 and 184 emerge. Here "position" is understood to be a location along the longitudinal axis of the bur head 162 relative to the distal end tip.

Each chamfer surface 196, 200, 202, and 204 is defined by at least two chamfer edges.

Chamfer surfaces 196 each have two chamfer edges 210 and 212. Starting at the most proximal location of each chamfer surface 196, cutting edge chamfer edge 210 starts at the distal end of the cutting edge 194 of flute 174 or 182 and extends generally linearly and distally forward. Chamfer edge 210 then arcuately curves to intersect, or abut, the respective chamfer surface 204 present on flute 172 or 180. Also starting at the distal end of the cutting edge of flute 174 or 182 is the chamfer edge 212. Distally forward of this point, edge 212 curves away from edge 210. Edge 210 curves until the edge 210 becomes the boundary between chamfer surface 196 and the adjacent chamfer surface 202. From this intersection of surface 192 and 202, edge 212 curves inwardly toward the distal end tip 163. The section of edge 212 intersects the point where surfaces 196, 200 and 202 meet. Distally forward of this point, edge forms the boundary between surfaces 196 and 200.

Each chamfer surface 200 is defined by two additional edges chamfer edges 214 and 216. Chamfer edge 214 extends from the from the point surfaces 196, 200 and 202 intersect to the point where surfaces 192 of flute 176 or 184 and surfaces 200 and 202 intersect. Chamfer edge 214 is generally linear in shape. Chamfer edge 216 forms the outer boundary of chamfer surface 200. Extends from the intersection of surface 192 of the flute 176 or 184 and surfaces 200 and 202 to the rake surface of the adjacent flute 178 or 170. Edge 216 is generally linear.

Two additional chamfer edges are present on the perimeter of each chamfer surface 202; a chamfer edge 218 and 220. Chamfer edge 202 starts where the clearance surface 192 of flute 174 or 182 and the adjacent chamfer surfaces 196 and 202 meet. From this point, chamfer edge 202 extends generally linearly to the distal end of the cutting edge of the associated with flute 176 or 184. Chamfer edge 220 starts at the proximal end terminus of chamfer edge 216. Chamfer edge 216 initially angles away from edge 218. Edge 218 then curves to and terminates at the point the cutting edge 194 and chamfer edge 218 meet.

Lastly, the chamfer surface 204 includes two chamfer edges 222 and 224. Chamfer edge 222 extends proximally from the distal end tip land to the cutting edge of the associated flute 172 or 180. Edge 222 is generally linear. Chamfer edge 222 starts at the intersection of the clearance surface 192 of the flute 172 or 180 and the adjacent chamfer surfaces 196 and 202. Initially, chamfer edge 224 angles away from edge 222. Edge 224 then curves toward edge 202. Chamfer edge 224 then terminates at the point cutting edge 194 and chamfer edge 202 meet.

The chamfer edge geometry of each chamfer surface 196, 200, 202, and 204 is not limited to the described version of the invention. It is purely a product of machining and chamfer surface size whether or not chamfer edges are shared or intersect one another. It is within the scope of the present invention to have chamfer surfaces that share fewer edges. Alternatively, one chamfer surface could extend radially around the entire surface of the bur head 162 in a fashion where small chamfer surfaces extend proximal to the large circumferential chamfer surface.

Figure 23:
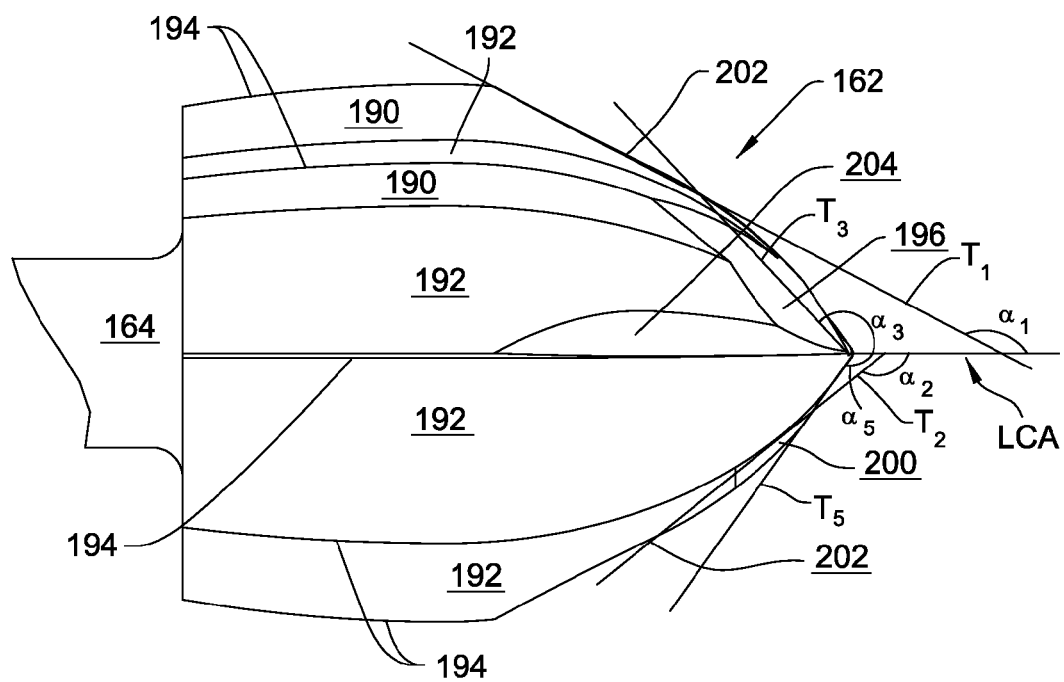
FIG. 23 is a side view of a bur head shaped in accordance with this invention, rotated along the axis of the bur, showing the pitch angles of the chamfer surfaces; and, FIG. 24 is a side view of a bur head shaped in accordance with this invention showing the pitch angles of the chamfer surfaces.
Figure 24:
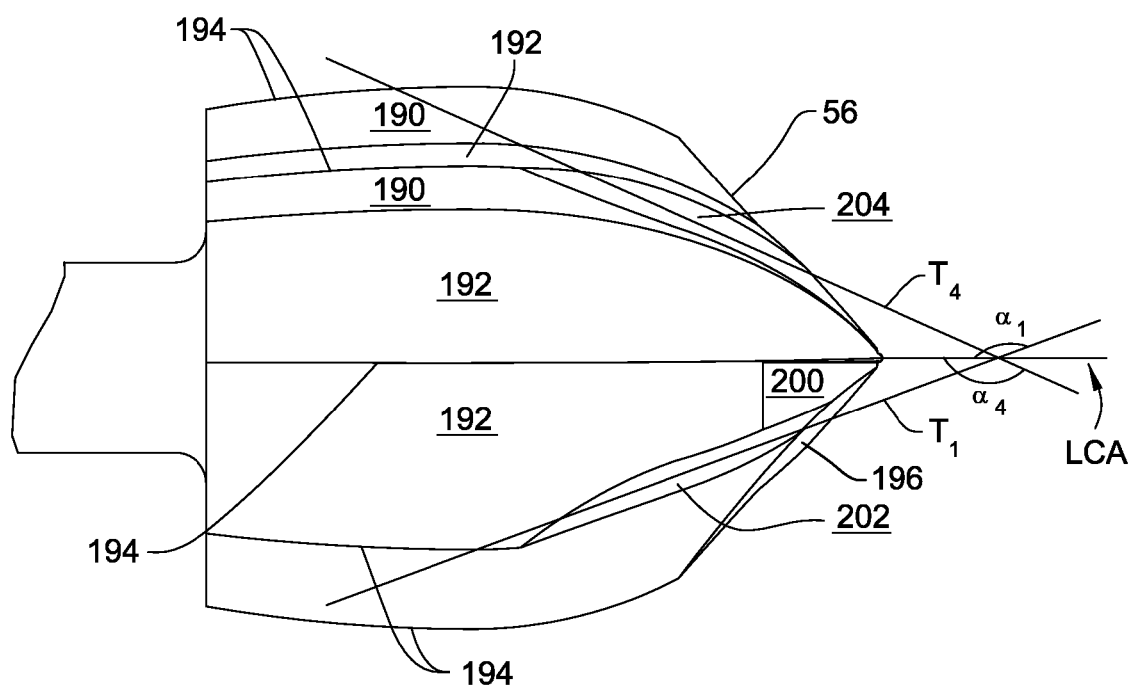

Another feature of the present invention relates to the angles of each chamfer surface 196, 200, 202, and 204 relative to the longitudinal center axis of the bur head 162. With respect to the below discussed FIGS. 23 and 24, these angles are shown by reference to a distal extension of this axis that extends forward of bur head tip 163. For the most part, each chamfer surface is not perfectly flat and is arcuate in nature. A tangent line extends from each chamfer surface. Each tangent line intersects either the bur head distal end tip 163 or a distal end extension of the longitudinal center axis (LCA). Each chamfer surface 196, 200, 202 and 204 can therefore be considered to have a chamfer angle which is the acute angle between the bur head longitudinal center axis and the tangent line of chamfer surface. In FIGS. 23 and 24, for ease of illustration, obtuse angles $\alpha 1$, $\alpha 2$, $\alpha 3$ and $\alpha 4$ that are complementary to the chamfer angles are called out. It is also noted, that though chamfer surface 196 looks flat, it is indeed curved. The radius of chamfer surface 196 is so large in nature that when such a portion of the radius is viewed, the surface visually looks flat. As can be seen in FIG. 24, both chamfer surfaces 202 and 204 have the tangent lines that are at the same angle relative to the distal end extension of the longitudinal center axis, of bur head 162. Thus, $\alpha 1$ equals $\alpha 4$. Tangent line T1 extends tangentially from the chamfer surface 202 intersecting the distal end extension of longitudinal center axis to create angle $\alpha 1$ therebetween. Likewise, tangent line T4 extends tangentially from the surface of chamfer surface 204 intersecting the distal end extension of the longitudinal center axis to create angle $\alpha 4$ therebetween. Since $\alpha 1$ equals $\alpha 4$, the chamfer surfaces 202 and 204 have the same chamfer angle relative to the distal end extension of the bur head longitudinal center axis.

FIG. 23 shows the relationship between $\alpha 1$, $\alpha 2$, $\alpha 3$, $\alpha 4$, and $\alpha 5$. As it has already been shown that $\alpha 1$ is equivalent to $\alpha 4$, for ease of illustration $\alpha 4$ is not depicted in FIG 23. As seen from FIGS. 23 and 24, each chamfer surface 196, 200, and 202 has a respective tangent line T3, T2 and T1, respectively, that it is at angle relative to the distal end extension of the bur head longitudinal center axis. Each tangent line T1, T2, and T3 intersects the distal end extension of the longitudinal center axis at an angle $\alpha 1$, $\alpha 2$ and $\alpha 3$, respectively. It can be seen that angle $\alpha 1$ and, by extension angle $\alpha 4$, are greater than $\alpha 2$. Angle $\alpha 4$ is greater than angle $\alpha 3$; which in turn is greater than $\alpha 5$. As stated above, angles $\alpha 1$ through $\alpha 4$ are the obtuse complements to the acute chamfer angles. Accordingly, the relationship between the chamfer angles of chamfer surfaces 196, 200, 202 and 204 are inverse from the above described angular relationships between the tangent lines and longitudinal center axis of the bur head. Chamfer surface 202 and, by extension, chamfer surface 204 have less of a chamfer angle in relationship to the longitudinal center axis of the bur head 162 than chamfer surface 200. Chamfer surface 200 has less of a chamfer angle than chamfer surface 196. The angles of the cutting edges of flutes 170 and 178 are represented by the line T5 and angle $\alpha 5$. Angle $\alpha 5$ has the greatest angle at the distal end tip 163 as compared to the angles of each chamfer surface 196, 200, 202, and 204. Angle $\alpha 5$ is less than angle $\alpha 1$. This means that the angle of the cutting edges of the chamferless flutes 170 and 178 adjacent the distal end tip relative to the longitudinal center axis of the bur head 162 is greater than the chamfer angles of the chamfer surface 196, 200, 202 and 204 associated with flutes 172, 174, 176, 180, 182 and 184.

As seen in FIG. 22, proximal from the distal end tip 163, where all the cutting edges 194 are present, bur head 162 is formed so that the cutting edges 164 are equangularly spaced apart.

Bur head 162 may be formed by first shaping the head to provide eight (8) identical flutes that extend the full length of the head from the distal end tip to the shaft. Then, portions of flutes 174 and 182 are selectively removed to form chamfer surfaces 196. Similarly, portions of flutes 172, 176, 180, and 184 are selectively removed to form chamfer surfaces 198. Grinding, electro-discharge machining or laser cutting or other machining methods may be employed to excise the material from flutes 172-36 and 180-184 to form their respective chamfer surfaces 196.

Alternatively formed, the bur head 162 may be formed by casting the bur head and grinding down the desired edges to form a cutting edge. By casting the bur head, the chamfer surfaces do not need to be grinded down due to the design of the cast.

When a surgeon applies a bur 160 to a surgical site, often the section of the bur adjacent the distal end tip 163 is the section of the bur head 162 that is pressed against the tissue to be excised. It is at this time the above-described geometry of the bur of this invention becomes advantageous. There are a reduced number of cutting edges 194 at the distal end tip 163, two that are symmetrical to one another in the preferred embodiment of an eight flute bur. This reduces the extent to which forces generated as a result of regeneration of waviness excite the bur into chatter vibration. Moreover, since there is a reduced number of cutting edges 194 at the most distal section of the bur head 162, the interstitial gap between cutting edges 194 is wider than it would be otherwise. The relatively large size of these gaps minimizes the extent to which excised tissue is trapped in these spaces. This reduces the extent to which tissue entrained in the inter-flute gaps imposes addition vibration-causing force on the bur head 162.

Since there are only two flutes 170 and 178 present at the location immediately proximal to the distal end tip 163, the tooth passing frequency at this location is very low. This further increases the likelihood that the low frequency tooth passing will matches and the chatter frequency and therefore cancels the chatter.

It should be recognized that the foregoing are particular embodiments of the invention. Other versions of the invention may have features different from what has been described. For example, in the disclosed version of the invention, the flutes with the short length cutting edges are alternate with the flutes having the longer length cutting edges. This feature of the invention need not be incorporated in all versions of the invention. Thus, in some versions of the invention a bur head may be arranged so that two or more long length cutting edges are followed by one or more flutes with shorter length cutting edges.

Similarly, in some burs of this invention, each pair of adjacent flutes with long length cutting edges may be separated by two or more flutes with shorter length cutting edges. In regard to these versions of the invention, there may be some applications wherein flutes with shorter length cutting edges are adjacent, one flute may formed to have a cutting edge of a first length and a adjacent short length flute formed to have a cutting edge of a second length. Thus, a bur head may be constructed to have, in sequence: a flute with a cutting edge that extends from the distal end tip of the head; a flute with chamfer surface 140; and a flute with chamfer surface 142.

Further, there is no requirement that the bur heads of this invention be constructed so that the different length cutting surfaces are symmetrically arranged around the outer perimeter of the bur head. For example a bur head with eight (8) cutting edges may be constructed so that where the individual cutting edges are all present, the edges are spaced 45° apart. In this version of the invention, the first, second, fourth, sixth and seventh flutes are constructed so as to have cutting edges that start adjacent the bur head distal end tip. The third, fifth and eighth flutes are constructed to have cutting edges that start at a position spaced proximally to where the first set of flutes start.

In the above version of the invention it may be provide the bur shaft with a feature that offsets the asymmetric structure of the bur head. Such feature may include one or more tabs or fingers that are extend outwardly from the body of the shaft. These tabs are asymmetrically positioned to offset the asymmetrical loading. Alternatively, this feature may comprise one or more pins embedded in the shaft that are flush with the shaft. These pins are of different density than the material forming the bur shaft and are again asymmetrically positioned to offset the asymmetric loading.

Figure 17:
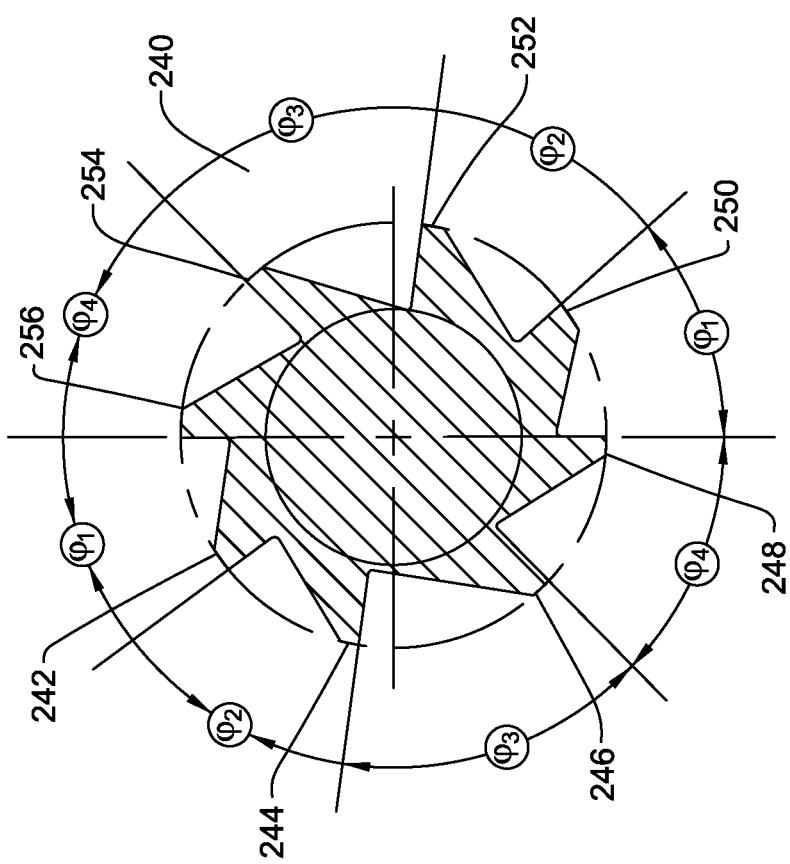
FIG. 17 is a cross sectional depiction of an alternative bur constructed in accordance with this invention.

FIG. 17 illustrates in cross section an alternative bur head 240 of this invention. Bur head 240 is shaped to have a number of arcuately spaced apart flutes 242-256. In this version of the invention flutes 242-256 may extend the complete length of the bur head 240, from the distal end tip to where the proximal end is joined to the shaft.

Bur head 240 is further formed so that around the circumference of the head, the flutes 242-256 are not equangularly spaced apart; the pitch angles between the adjacent flute pairs are different. For example, in the illustrated version of the invention flutes 242-256 and 248-250 are spaced apart angle $\phi_1=38°$. Adjacent flutes 242-244 and 250-252 are spaced apart angle $\phi_2=43°$. Adjacent flutes 244-246 and 252-254 are spaced apart angle $\phi_3=52°$. Adjacent flutes 246-248 and 254-256 are spaced apart angle $\phi_4=47°$.

When the bur having this head geometry is employed, the between two adjacent pairs of flutes, for example between adjacent flutes 244-246 and 246-248, the time between when each flute in the pair strikes the tissue is different. Thus in the above example the time between when flute 246 strikes the bone after it is first struck by flute 244 is less than the time between when flute 248 strikes the bone after it is initially struck by flute 246. This variable periodicity between flute strikes is believed to reduce the extent the bur is forced into chatter-causing vibration.

This feature of the invention may or may not be incorporated into the versions of the invention with variable length cutting edges. Also, the bur head of this invention may be constructed so that not all adjacent pairs of the flutes have pitch angles that vary from each other. Thus, for example with a bur having eight flutes, there may be a first pitch angle between 6 of the adjacent flute pairs and a second pitch angle between two of the adjacent flute pairs It should likewise be appreciated that the disclosed basic bur head shapes are exemplary, not limiting. In alternative versions of the invention, the bur heads may have alternative shapes including barrel head, conical, egg, pear or drum shaped. Thus, there in some versions of the invention, the distal end tips of the bur heads may have profiles different than the curved convex profile of the illustrated embodiments.

Likewise, there is no requirement that, in all versions of the invention, the shorter length cutting edges emerge at the location where the bur heads reach there maximum diameter. The shorting length cutting edges are fully emerged at positions along the bur head distal to where the bur head has its larges diameter.

Also, in some versions of the invention, the flutes with the shorter length cutting edges may have shorter length cutting edges by virtue of the cutting edges terminating at a position along the bur head spaced distally from the locations along which other cutting edges terminate. Some versions of the invention may be constructed so that, between flutes with cutting edges that extend the full length of the bur head, there are flutes with cutting edges that start a position proximal to the bur head distal end tip and terminate at a position distal to the proximal terminus of the bur head.

Further while two means of shaping the bur to provide cutting edges of different lengths are shown, it other versions of this invention may have different flute arrangements and flute shapes to provide the same structural features. Also, flutes of different shapes may be provided on a single bur. Thus, a single bur may have: a first set of flutes that are relatively long and shaped with relatively long cutting edges; a second set of flutes that are also relatively long and shaped with chamfered surfaces to have short cutting edges; and a third set of one or more flutes that are relatively short in length.

The various features of the different versions of the bur of this can be combined as appropriate. Thus the bur of FIG. 18, with only two flutes that fully emerge from the distal end tip may be combined with the bur having variable pitches between flutes of FIG. 17.

It is likewise understood that the shaft structure is not limited to what has been disclosed. The bur of this invention may have a tubular shaft. In these versions of the invention the shaft typically has an opening immediately proximal to the bur head. The opening functions as a port through which irrigating fluid is discharged or a suction is drawn. In these versions of the invention, the coupling feature of the bur is often a hub attached to the proximal open end of the shaft. The hub has both geometric features that facilitate the coupling of the bur to a drive handpiece and a port to establish fluid communication to a suction device or from a source of irrigating fluid.

Thus, it is an object of the appended claims to cover all such variations and modifications that come within the true spirit and scope of this invention.

What is claimed is:
1. A surgical bur, said bur including:
an elongated shaft having opposed proximal and distal ends;
a coupling feature associated with the proximal end of said shaft, the coupling featured shaped to engage a drive unit of a surgical handpiece so that the handpiece can rotate said shaft;

a bur head attached to the distal end of said shaft, the bur head having: a body with a distal end tip; a longitudinal axis that extends through the body including through the distal end tip; and a plurality of flutes that emerge from said body, wherein each said flute has a rake surface and a clearance surface that meet to define a cutting edge that extends radially beyond said shaft wherein:

a single pair of first flutes that are symmetric to each other around the body distal end tip and that emerge from said bur head body distal end tip so as to have cutting edges that extend proximally from a distal position that is located adjacent said bur head body distal end tip and wherein said flutes forming the pair of first flutes are separated from each other by opposed arcuate sections of said bur head body;

a single pair of second flutes that are symmetric to each other around said bur head body distal end tip, wherein said flutes forming the pair of second flutes emerge from separate arcuate sections of said bur head body;

two pairs of third flutes, the pairs of the third flutes positioned so that: said flutes forming each pair of third flutes emerge from separate arcuate sections of said bur head body; one of said flute pairs of said third flutes are symmetric around said bur head body distal end tip; and each third flute is located between one of the first flutes and one of the second flutes;

first chamfer surfaces extend proximally from adjacent said bur head body distal end tip, each said first chamfer surface forming a distal end face of one of the second flutes and the third flutes adjacent the second flute so that the each second flute has cutting edge that extends proximally from a position along the bur head that is spaced proximal to the distal end tip, and the first chamfer surfaces are at a first chamfer angle relative to the bur head longitudinal axis; and a second chamfer surface extends over each third flute, the second chamfer surfaces extending proximally relative to the first chamfer surfaces and being at a second chamfer angle relative to the bur head longitudinal axis, the second chamfer angle being less than the first chamfer angle so that each third flute has a cutting edge that extends distally from a position along the bur head that is spaced proximal to the position from which the cutting edges of the second flutes extend proximally.

2. The surgical bur of claim 1, wherein each second chamfer surface abuts one of the first chamfer surfaces.

3. The surgical bur of claim 1, wherein, within each arcuate section of said bur head body between the first flutes:

a first one of the second chamfer surfaces extends over a first one of the third flutes and the first one of the second chamfer surfaces extends proximally from a position proximal to the bur head body distal end tip; and a second one of the second chamfer surfaces extends over a second one of the third flutes and extends proximally from a position that is spaced proximally away from the bur head body distal end tip.

4. The surgical bur of claim 3, wherein, within each arcuate section of said bur head body between said first flutes, a third chamfer surface separate from the first chamfer surface and the second chamfer surfaces extends over the second one of the third flutes, the third chamfer surface being closer to the bur head body distal end tip than the second one of the second chamfer surfaces.

5. The surgical bur of claim 1, wherein said coupling feature associated with the proximal end of said shaft includes at least one from the group consisting of: a recess that extends inwardly relative to an outer diameter of said shaft; and a tab that projects outwardly from said shaft.

6. A surgical bur, said bur including:

an elongated shaft having opposed proximal and distal ends;

a coupling feature associated with the proximal end of said shaft, the coupling featured shaped to engage a drive unit of a surgical handpiece so that the handpiece can rotate said shaft; and a bur head attached to the distal end of said shaft, the bur head having: a body with a distal end tip; and a plurality of flutes that emerge from said body and that extend outwardly of said shaft, each said flute having a rake surface and a clearance surface that meet to define a cutting edge, said flutes shaped so that said cutting edges extend radially beyond said shaft, wherein:

a single pair of first flutes that are symmetric with each other relative to the bur head body distal end tip emerge from said body so as to have cutting edges that extend proximally from a location adjacent the body distal end tip and the first flutes are separated from each other by opposed arcuate sections of said bur head body;

three second flutes emerge from said bur head body in each of the arcuate sections of said bur head body between the first flutes wherein two of said second flutes are symmetric with two second flutes in the opposed arcuate section; and in each arcuate section of said bur head body between the first flutes a plurality of chamfer surfaces extend over the second flutes wherein two of the chamfer surfaces are at different chamfer angles relative to a longitudinal center axis through the bur head and wherein a first one of the two chamfer surfaces extends over a plurality of the second flutes and a second one of the two chamfer surfaces does not extend over each of the flutes over which the first chamfer surfaces extends, the chamfer surfaces being further disposed over the second flutes so that:

said second flutes have cutting edges that extend proximally from locations on said bur head that are spaced proximal to the location from which the cutting edges of said first flutes extend proximally; and a first one of said second flutes within each arcuate section of said bur head body has a cutting edge that extends proximally from a first location on said bur head, the first location being proximal to the location from which the cutting edges of said first said flutes extend proximally, and the second and third flutes of second flutes within each arcuate section each has a cutting edge that extends proximally from a second location on said bur head, the second location being spaced proximal to the first location.

7. The surgical bur of claim 6, wherein, in each arcuate section of said bur head body between the first flutes the two chamfer surfaces that are at different chamfer angles border each other.

8. The surgical bur of claim 6, wherein, in each arcuate section of said bur head body between the first flutes at least one chamfer surface extends over a single one of the second flutes.

9. The surgical bur of claim 6, wherein, in each arcuate section of said bur head body between the first flutes:

there are two second flutes that are arcuately adjacent the first flutes and there is a single second flute that is arcuately spaced from the first flute, the single second flute being located between the two second flutes that are arcuately adjacent the first flutes; and the chamfer surfaces are further disposed over the second flutes so that, within each arcuate section, the second flutes arcuately adjacent the first flutes having cutting edges that extend proximally from a location on said bur head that is proximal to the location on said bur head from which the cutting edge of the single second flute that is arcuately spaced from the first flutes extends proximally.

10. The surgical bur of claim 6, wherein said coupling feature associated with the proximal end of said shaft includes at least one from the group consisting of: a recess that extends inwardly relative to an outer diameter of said shaft; and a tab that projects outwardly from said shaft.

11. The surgical bur of claim 6, wherein, in each arcuate section of said bur head body between the first flutes:
  there are two second flutes that are arcuately adjacent the first flutes and there is a single second flute that is arcuately spaced from the first flute, the single second flute being located between the two second flutes that are arcuately adjacent the first flutes; and
  the chamfer surfaces are further disposed over the second flutes so that, within each arcuate section: a first one of the chamfer surfaces extends over each of the second flutes; a second one of the chamfer surfaces only extends over a first one of the second flutes that is arcuately adjacent one of the first flutes; and a third chamfer surface only extends over a second one of the second flutes that is arcuately adjacent the second one of the flutes and the chamfer surfaces are at different chamfer angles so that the second flutes arcuately adjacent the first flutes having cutting edges that extend proximally from a location on said bur head that is proximal to the location on said bur head from which the cutting edge of the single second flute that is arcuately spaced from the first flutes extends proximally.

12. The surgical bur of claim 11, wherein, in each arcuate section of said bur head body between the first flutes, the chamfer angle of the second and third chamfer surfaces are equal.

13. The surgical bur of claim 11, wherein, in each arcuate section of said bur head body between the first flutes, there is a fourth chamfer surface that extends over one of the second flutes that is arcuately adjacent one of the first flutes.

14. The surgical bur of claim 13, wherein in each arcuate section of said bur head body, the fourth chamfer surface abuts the first chamfer surface.

15. The surgical bur of claim 11, wherein in each arcuate section of said bur head body: the first chamfer surface has first and second opposed sides; the second chamfer surface abuts a first side of the first chamfer surface.

16. The surgical bur of claim 15, wherein the third chamfer surface abuts the second side of the first chamfer surface.

* * * * *